United States Patent
Evans et al.

(10) Patent No.: US 11,497,490 B2
(45) Date of Patent: Nov. 15, 2022

(54) POWERED SURGICAL DEVICES INCLUDING PREDICTIVE MOTOR CONTROL

(71) Applicant: Covidien LP, Mansfield, MA (US)

(72) Inventors: Christopher Kelly Evans, Southington, CT (US); Thomas Wingardner, North Haven, CT (US)

(73) Assignee: Covidien LP, Mansfield, MA (US)

( * ) Notice: Subject to any disclaimer, the term of this patent is extended or adjusted under 35 U.S.C. 154(b) by 187 days.

(21) Appl. No.: 16/441,508

(22) Filed: Jun. 14, 2019

(65) Prior Publication Data
US 2020/0008798 A1  Jan. 9, 2020

Related U.S. Application Data

(60) Provisional application No. 62/695,421, filed on Jul. 9, 2018.

(51) Int. Cl.
*A61B 17/00* (2006.01)
*A61B 17/068* (2006.01)
(Continued)

(52) U.S. Cl.
CPC .......... *A61B 17/068* (2013.01); *A61B 17/115* (2013.01); *A61B 17/282* (2013.01);
(Continued)

(58) Field of Classification Search
CPC ............... A61B 17/068; A61B 17/115; A61B 17/282; A61B 2017/00221; A61B 2017/00393;
(Continued)

(56) References Cited

U.S. PATENT DOCUMENTS

| 37,165 A | 12/1862 | Gary |
| 3,209,754 A | 10/1965 | Brown |

(Continued)

FOREIGN PATENT DOCUMENTS

| CN | 101683284 A | 3/2010 |
| CN | 102648864 A | 8/2012 |

(Continued)

OTHER PUBLICATIONS

European Search Report issued in corresponding European Application No. 19184928.0 dated Nov. 12, 2019, 7 pages.

*Primary Examiner* — Robert F Long
(74) *Attorney, Agent, or Firm* — Carter, DeLuca & Farrell LLP

(57) ABSTRACT

A powered handheld electromechanical surgical device includes a motor configured to drive extension and retraction of a drive component, a sensor configured to sense force exerted on the drive component during extension of the drive component, and a controller including a processor and a non-transitory computer-readable storage medium storing instructions that, when executed by the processor, cause the processor to receive the sensed force from the sensor, control a speed of the motor during extension of the drive component in accordance with the sensed force, determine a speed profile or a force profile during extension of the drive component, and control a speed of the motor during retraction of the drive component in accordance with the speed profile or the force profile.

11 Claims, 5 Drawing Sheets

(51) Int. Cl.
    *A61B 17/115*     (2006.01)
    *A61B 17/28*     (2006.01)
    *A61B 17/072*     (2006.01)

(52) U.S. Cl.
    CPC .............. *A61B 2017/00221* (2013.01); *A61B 2017/00393* (2013.01); *A61B 2017/00398* (2013.01); *A61B 2017/00464* (2013.01); *A61B 2017/00473* (2013.01); *A61B 2017/00486* (2013.01); *A61B 2017/00734* (2013.01); *A61B 2017/07257* (2013.01); *A61B 2017/07271* (2013.01)

(58) Field of Classification Search
    CPC ........... A61B 2017/00398; A61B 2017/00464; A61B 2017/00473; A61B 2017/00486; A61B 2017/00734; A61B 2017/07257; A61B 2017/07271; A61B 2017/00017; A61B 2017/0046; A61B 17/07207; A61B 17/072; A61B 90/06; A61B 2017/00367; A61B 2017/00137; A61B 2090/064
    USPC ....................... 227/175.1–182.1; 606/75, 219
    See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,775,945 A * | 10/1988 | Cavill .................... B41J 19/202 318/569 |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |

(56) References Cited

U.S. PATENT DOCUMENTS

| | | |
|---|---|---|
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |

(56) References Cited

U.S. PATENT DOCUMENTS

| | | |
|---|---|---|
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,819,896 B2 | 10/2010 | Racenet |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 9,764,357 B2 * | 9/2017 | Houston ............... B06B 1/166 |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0049219 A1* | 3/2004 | Briggs ............... A61B 5/15123 606/181 |
| 2004/0122292 A1* | 6/2004 | Dey ............... A61B 1/0684 600/190 |
| 2004/0232201 A1 | 11/2004 | Wenchell et al. |
| 2005/0006429 A1 | 1/2005 | Wales et al. |

(56) References Cited

U.S. PATENT DOCUMENTS

| | | |
|---|---|---|
| 2005/0010235 A1 | 1/2005 | VanDusseldorp |
| 2005/0090740 A1* | 4/2005 | Raitzer .................. A61B 8/12 600/437 |
| 2005/0116673 A1* | 6/2005 | Carl .................. A61B 17/1626 318/432 |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2006/0151567 A1* | 7/2006 | Roy .................... A61B 17/115 227/175.1 |
| 2006/0156876 A1* | 7/2006 | Sussmeier ............. B65H 35/06 83/13 |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1* | 8/2007 | Shelton .................. A61B 34/76 227/176.1 |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2007/0270790 A1* | 11/2007 | Smith .................... A61B 90/03 606/1 |
| 2008/0021490 A1* | 1/2008 | Briggs ............ A61B 5/150152 606/181 |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2008/0262476 A1* | 10/2008 | Krause ............. A61B 17/32002 604/540 |
| 2009/0012556 A1* | 1/2009 | Boudreaux ........... A61B 90/06 600/587 |
| 2009/0018624 A1 | 1/2009 | Levinson et al. |
| 2009/0024142 A1* | 1/2009 | Ruiz Morales ........ A61B 34/35 606/130 |
| 2009/0054909 A1* | 2/2009 | Farritor .................. A61B 34/70 606/130 |
| 2009/0065258 A1* | 3/2009 | Hamilton ................ E21B 7/06 175/61 |
| 2009/0090201 A1 | 4/2009 | Viola |
| 2009/0090763 A1 | 4/2009 | Zemlok et al. |
| 2009/0108048 A1* | 4/2009 | Zemlok ............ A61B 17/00234 227/175.1 |
| 2009/0270896 A1* | 10/2009 | Sullivan .......... A61B 17/320016 606/170 |
| 2010/0001036 A1* | 1/2010 | Marczyk .......... A61B 17/07207 227/175.1 |
| 2010/0163023 A1* | 7/2010 | Singh ............... A61M 16/0438 128/200.26 |
| 2010/0200636 A1 | 8/2010 | Zemlok et al. |
| 2010/0270355 A1* | 10/2010 | Whitman ............. A61B 17/068 227/176.1 |
| 2010/0312257 A1 | 12/2010 | Aranyi |
| 2010/0320254 A1 | 12/2010 | Zemlok et al. |
| 2011/0022032 A1* | 1/2011 | Zemlok ........... A61B 17/07207 606/1 |
| 2011/0034910 A1 | 2/2011 | Ross et al. |
| 2011/0062211 A1 | 3/2011 | Ross et al. |
| 2011/0125138 A1* | 5/2011 | Malinouskas ........ A61B 90/90 606/1 |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0116379 A1* | 5/2012 | Yates .................... G16H 40/63 606/33 |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1* | 9/2012 | Viola .................. A61B 17/072 227/175.1 |
| 2012/0241494 A1 | 9/2012 | Marczyk |
| 2012/0248167 A1* | 10/2012 | Flanagan ............... A61B 34/30 227/2 |
| 2012/0277790 A1 | 11/2012 | Zemlok et al. |
| 2012/0298718 A1 | 11/2012 | Marczyk |
| 2012/0298720 A1 | 11/2012 | Marczyk |
| 2013/0018400 A1* | 1/2013 | Milton .................. A61B 90/06 606/167 |
| 2013/0116668 A1* | 5/2013 | Shelton, IV .......... A61B 34/76 606/1 |
| 2013/0321262 A1* | 12/2013 | Schecter ................ A61B 34/76 345/156 |
| 2013/0324999 A1* | 12/2013 | Price .............. A61B 17/320092 606/41 |
| 2014/0012289 A1 | 1/2014 | Snow et al. |
| 2014/0142507 A1* | 5/2014 | Armes .................... A61M 5/20 604/112 |
| 2014/0166323 A1* | 6/2014 | Cooper .................. F16P 3/148 173/1 |
| 2014/0171923 A1 | 6/2014 | Aranyi |
| 2014/0194250 A1* | 7/2014 | Reich ................ A63B 24/0062 482/5 |
| 2014/0263538 A1* | 9/2014 | Leimbach .......... A61B 17/0686 227/175.1 |
| 2014/0291382 A1* | 10/2014 | Lloyd ............... A61B 17/07292 227/176.1 |
| 2015/0053749 A1* | 2/2015 | Shelton, IV ............ H02J 7/342 227/181.1 |
| 2015/0054753 A1* | 2/2015 | Morgan ............... A61B 17/072 345/173 |
| 2015/0080912 A1* | 3/2015 | Sapre ............... A61B 17/07207 606/139 |
| 2015/0122870 A1* | 5/2015 | Zemlok ............ A61B 17/07207 227/176.1 |
| 2015/0209059 A1* | 7/2015 | Trees .................. A61B 18/1445 606/170 |
| 2015/0272575 A1* | 10/2015 | Leimbach ............. A61B 90/98 227/175.3 |
| 2015/0351765 A1* | 12/2015 | Valentine ............ G06F 11/1448 227/176.1 |
| 2016/0128704 A1* | 5/2016 | McGinley .......... A61B 17/1626 606/80 |
| 2016/0242779 A1* | 8/2016 | Aranyi ................. A61B 17/068 |
| 2016/0278872 A1* | 9/2016 | Gombert ................ A61B 34/72 |
| 2016/0310134 A1 | 10/2016 | Contini et al. |
| 2017/0079640 A1* | 3/2017 | Overmyer ................ H02P 7/06 |
| 2017/0095897 A1* | 4/2017 | Moraru ................ B23Q 15/0075 |
| 2017/0105614 A1* | 4/2017 | McWilliam ....... A61M 16/0488 |
| 2017/0202591 A1* | 7/2017 | Shelton, IV .......... A61B 18/00 |
| 2017/0202605 A1* | 7/2017 | Shelton, IV ... A61B 17/320068 |
| 2017/0202607 A1* | 7/2017 | Shelton, IV ............ H02J 50/10 |
| 2017/0215720 A1* | 8/2017 | Walker .................... A61B 1/267 |
| 2017/0245854 A1 | 8/2017 | Zemlok et al. |
| 2017/0249431 A1* | 8/2017 | Shelton, IV ........... H01M 10/48 |
| 2018/0132850 A1* | 5/2018 | Leimbach .............. A61B 90/96 |
| 2018/0250002 A1* | 9/2018 | Eschbach ......... A61B 17/07207 |
| 2018/0250004 A1* | 9/2018 | Williams ............. A61B 17/072 |
| 2018/0318133 A1* | 11/2018 | Clauson ............ A61B 17/22031 |
| 2018/0345972 A1* | 12/2018 | Turkoglu ............. B60W 30/143 |
| 2018/0360473 A1* | 12/2018 | Shelton, IV ...... A61B 17/07207 |
| 2019/0183494 A1* | 6/2019 | Shelton, IV ...... A61B 17/07207 |
| 2019/0183503 A1* | 6/2019 | Shelton, IV ...... A61B 17/07207 |
| 2019/0201034 A1* | 7/2019 | Shelton, IV .......... A61B 18/00 |

(56) References Cited

U.S. PATENT DOCUMENTS

2020/0107898 A1\* 4/2020 Kim ................ A61B 1/018
2020/0360041 A1\* 11/2020 Marinkovic ..... A61B 17/32002
2020/0375447 A1\* 12/2020 Kotamarti .......... A61B 1/00055

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 2954854 A2 | 12/2015 |
| EP | 3231373 A2 | 10/2017 |
| FR | 2 849 589 A1 | 7/2004 |
| WO | 20199414129 A1 | 6/1994 |
| WO | 20199729694 A1 | 8/1997 |
| WO | 20199740760 A1 | 11/1997 |
| WO | 20199837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004/032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |

\* cited by examiner

POWERED SURGICAL DEVICES INCLUDING PREDICTIVE MOTOR CONTROL

CROSS-REFERENCE TO RELATED APPLICATIONS

This application claims the benefit of and priority to U.S. Provisional Patent Application No. 62/695,421 filed Jul. 9, 2018, the entire disclosure of which is incorporated by reference herein.

TECHNICAL FIELD

The present disclosure relates generally to surgical devices. More particularly, the present disclosure relates to powered handheld electromechanical surgical devices.

BACKGROUND

A number of manufacturers have developed surgical devices incorporating powered drive systems for operating and/or manipulating an end effector at a distal end of the device. In many instances, the surgical devices include a powered handle assembly that is reusable and a end effector that is selectively connected to the powered handle assembly prior to use and then disconnected therefrom following use in order to be disposed of or, in some instances, sterilized for re-use.

The use of powered surgical devices such as, for example, electromechanical surgical staplers, has grown tremendously over the past few decades. Advanced technologies and informatics within these intelligent devices provide the ability to gather clinical and operational data that can be used to improve performance, drive design improvements and, ultimately, improve patient outcomes.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

Provided in accordance with aspects of the present disclosure is a powered handheld electromechanical surgical device including a motor configured to drive extension and retraction of a drive component, a sensor configured to sense force exerted on the drive component during extension of the drive component, and a controller including a processor and a non-transitory computer-readable storage medium. The storage medium stores instructions that, when executed by the processor, cause the processor to receive the sensed force from the sensor, control a speed of the motor during extension of the drive component in accordance with the sensed force, determine a speed profile and/or a force profile during extension of the drive component, and control a speed of the motor during retraction of the drive component in accordance with the speed profile and/or the force profile.

In an aspect of the present disclosure, the powered handheld electromechanical surgical device according further includes a handle assembly including the motor and controller disposed therein, and an adapter assembly releasably engaged with the handle assembly and including the drive component and sensor disposed therein.

In another aspect of the present disclosure, the powered handheld electromechanical surgical device further includes an end effector releasably engaged with the adapter assembly. In such aspects, extension of the drive component at least one of closes or fires the end effector and retraction of the drive component opens the end effector.

In yet another aspect of the present disclosure, the sensor is a strain gauge.

In still another aspect of the present disclosure, the motor provides a rotational output. The rotational output is converted into translation of the drive component to extend and retract the drive component.

A method of controlling a powered handheld electromechanical surgical device provided in accordance with aspects of the present disclosure includes activating a motor to drive extension of a drive component, sensing force exerted on the drive component during extension of the drive component, controlling a speed of the motor during extension of the drive component in accordance with the sensed force, determining one of speed profile during extension of the drive component or a force profile during extension of the drive component, and controlling a speed of the motor during retraction of the drive component in accordance with the speed profile or the force profile.

BRIEF DESCRIPTION OF THE DRAWINGS

Aspects and features of the present disclosure are described in detail with reference to the drawing figures wherein like reference numerals identify similar or identical structural elements and.

DETAILED DESCRIPTION

Figure 1:
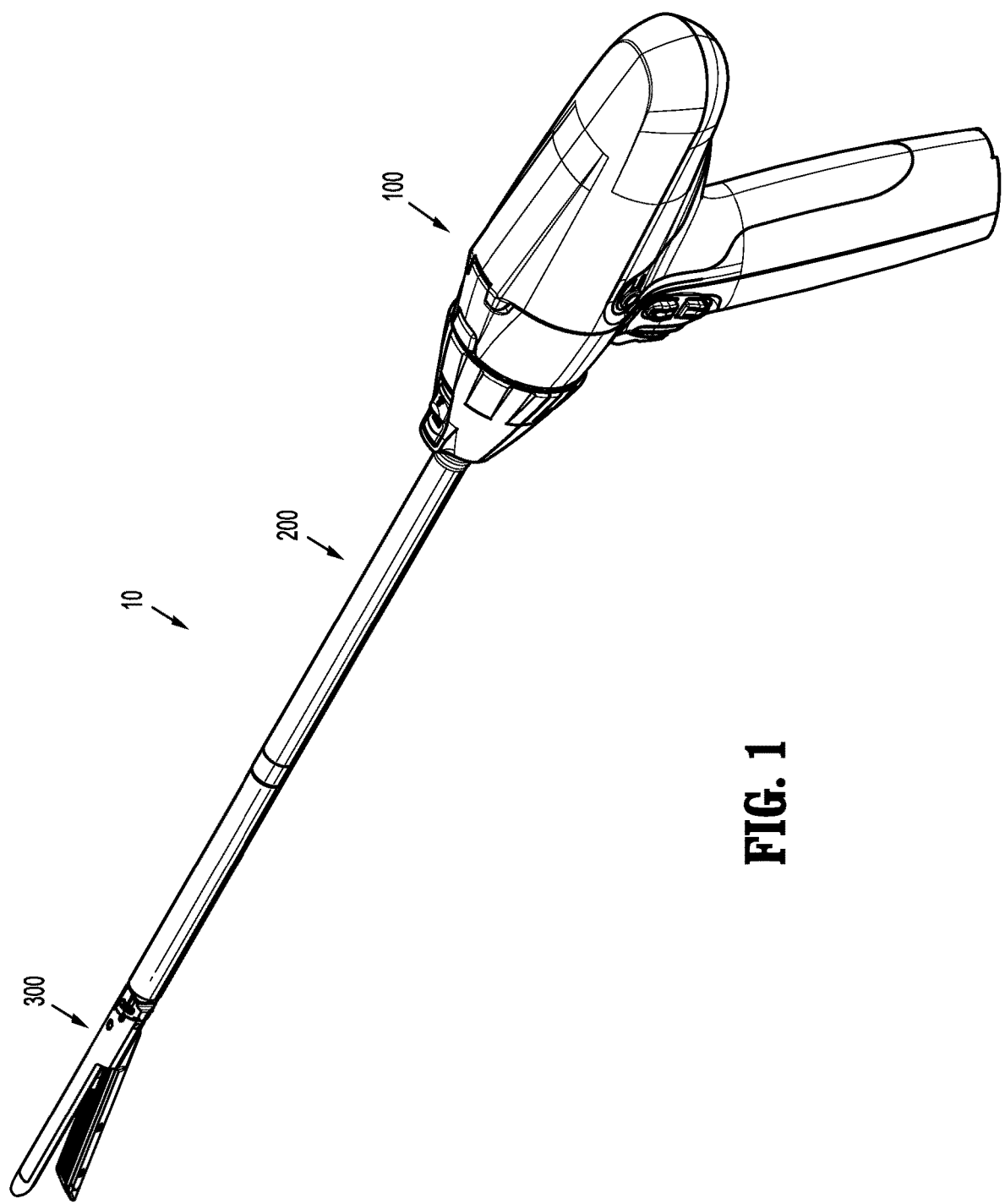
FIG. 1 is a perspective view of a surgical device configured for use in accordance with the present disclosure and including a handle assembly, an adapter assembly, and an end effector.

Turning to FIG. 1, a powered handheld electromechanical surgical device exemplifying the aspects and features of the present disclosure is shown generally identified by reference numeral 10. Surgical device 10 includes a handle assembly 100, an adapter assembly 200, and an end effector 300. Handle assembly 100 is configured for selective connection with adapter assembly 200 and, in turn, adapter assembly 200 is configured for selective connection with end effector 300. Although detailed herein with respect to surgical device 10, it is understood that the aspects and features of the present disclosure apply equally to any suitable powered handheld electromechanical surgical device. Thus, surgical device 10 is detailed herein only to the extent necessary to exemplify the aspects and features of the present disclosure. A more detailed description of surgical device 10 can be found in commonly owned U.S. Patent Appl. Pub. No.

2016/0310134, the entire contents of which are hereby incorporated herein by reference.

Figure 2:
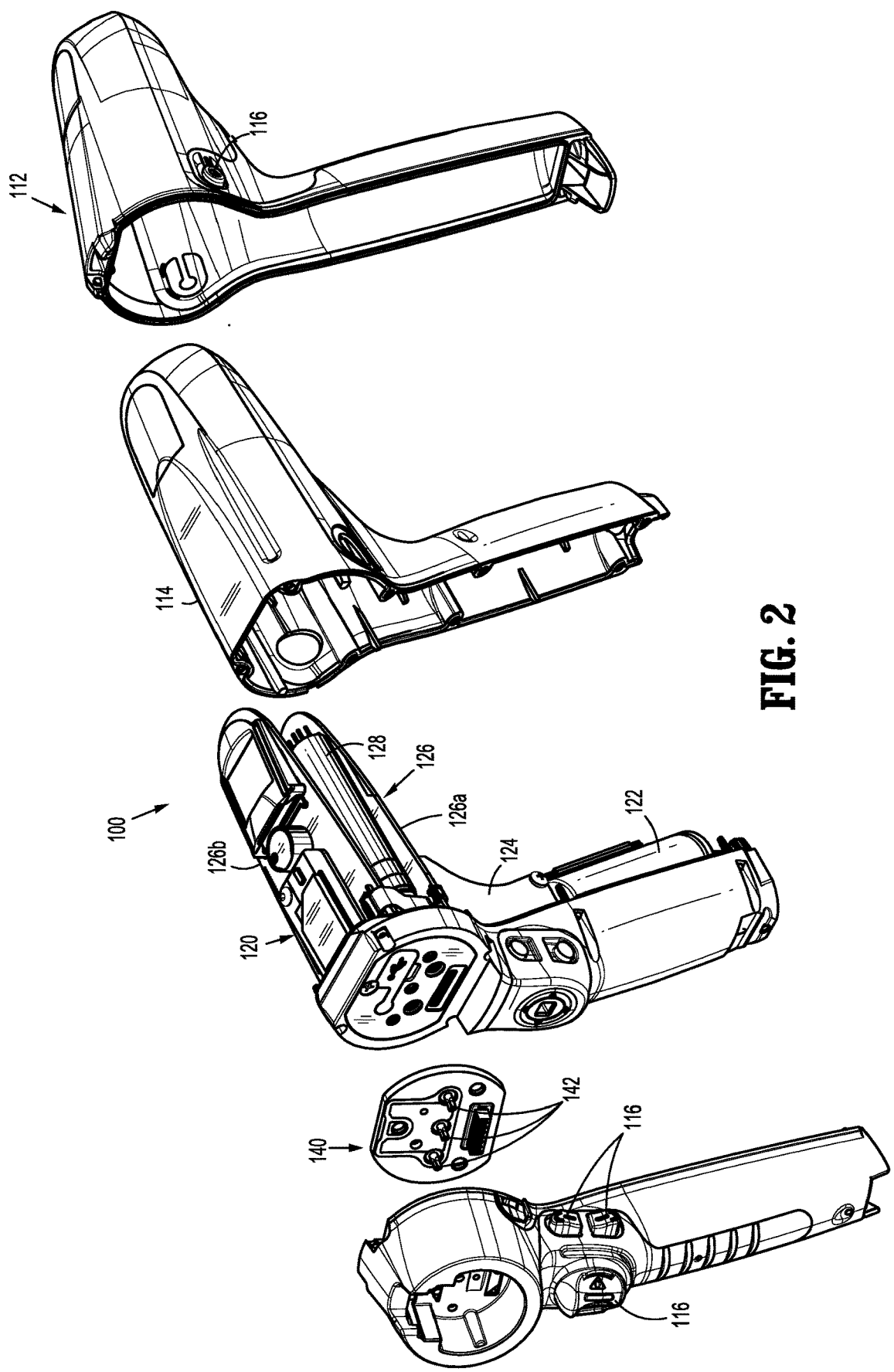
FIG. 2 is a perspective view, with parts separated, of the handle assembly of the surgical device of FIG. 1.

Referring also to FIG. 2 handle assembly 100 generally includes an outer housing shell 112, an inner handle housing 114 disposed within outer housing shell 112, and a power-pack 120 disposed within inner handle housing 114 for powering and controlling the various operations of surgical device 10. A plurality of actuators 116 (e.g., finger-actuated control buttons, knobs, toggles, slides, interfaces, and the like) disposed on outer housing shell 112 communicate with power-pack 120 to enable user-controlled activation of power-pack 120 to perform the various operations of surgical device 10.

Power-pack 120 includes a rechargeable battery 122 configured to supply power to surgical device 10, a battery circuit board 124 (including at least one processor and associated memory), and a controller circuit board 126. Controller circuit board 126 includes a motor controller circuit board 126a (including at least one processor and associated memory) and a main controller circuit board 126b (including at least one processor and associated memory) operably coupled with one another. Motor controller circuit board 126a is operably coupled with battery circuit board 124 enabling communication therebetween and between battery circuit board 124 and main controller circuit board 126b.

Power-pack 120 further includes one or more motors 128 each electrically connected to controller circuit board 126 and battery 122. Each motor 128 includes a respective motor shaft (not shown) extending therefrom for transmitting rotative forces and is controlled by a respective motor controller disposed on motor controller circuit board 126a to enable independent control of each motor 128. Rotation of each motor shaft by its respective motor 128 functions to drive corresponding components of the adapter assembly 200 in order to perform the various operations of surgical device 10, as detailed below. The motor shaft of each motor 128, more specifically, is configured to cooperate with an output shaft 142 of a plate assembly 140 of handle assembly 100 to provide a rotational output from handle assembly 100 to adapter assembly 200.

Figure 3:
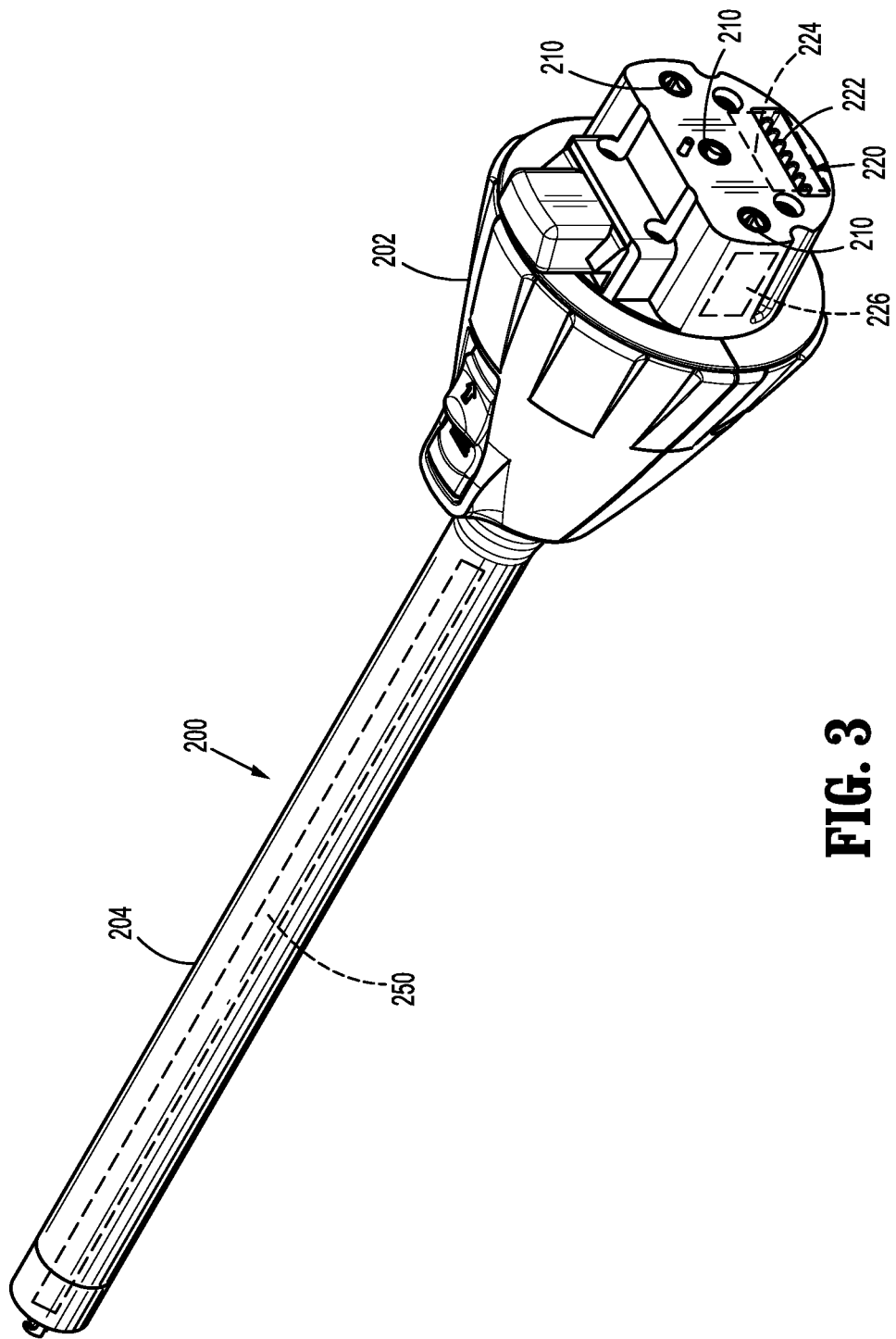
FIG. 3 is a perspective view of the adapter assembly of the surgical device of FIG. 1.

Referring to FIG. 3, in conjunction with FIGS. 1 and 2, adapter assembly 200 includes a connector housing 202 and an outer tube 204 extending distally from connector housing 202. Connector housing 202 is configured for operable connection to handle assembly 100 and the distal end portion of outer tube 204 is configured for operable connection to end effector 300. Adapter assembly 200 further includes one or more rotatable connectors 210 each extending proximally from connector housing 202 and configured to operably couple to a corresponding motor shaft of handle assembly 100 by way of a corresponding output shaft 142 of plate assembly 140 of handle assembly 100 to enable independent rotation of each connector 210 by a respective motor 128, such that rotational force(s) may be selectively transferred from motor(s) 128 of handle assembly 100 to adapter assembly 200. Adapter assembly 200 further includes one or more force/rotation transmitting/converting assemblies (not shown), each extending through connector housing 202 and outer tube 204 and operably coupled to one of the connectors 210. For example, a first force/rotation transmitting/converting assembly may be provided to convert a rotational input from a first of the motors 128 to a first connector 210 into axial translation of an articulation bar (not shown) of adapter assembly 200 to effectuate articulation of end effector 300, a second force/rotation transmitting/converting assembly may be provided to convert a rotational input from a second of the motors 128 to a second connector 210 into rotation of a ring gear (not shown) of adapter assembly 200 to effectuate rotation of adapter assembly 200, and thus, end effector 300, and a third force/rotation transmitting/converting assembly may be provided to convert a rotational input 210 from a third of the motors 128 to a third connector 210 into axial translation of a drive component, e.g., a distal drive member 250 of adapter assembly 200, to effectuate closing, opening, and firing of end effector 300.

An electrical assembly 220 of adapter assembly 200 is supported by connector housing 202 and includes a plurality of electrical contacts 222 extending from a circuit board 224 for electrical connection to handle assembly 100. Electrical assembly 220 also includes a strain gauge 226 electrically connected to circuit board 224, e.g., at least one processor and associated memory thereof, for feedback of closing/firing loads exhibited by adapter assembly 200, e.g., force feedback regarding the distal translation of the distal drive member 250 of adapter assembly 200 to close and fire end effector 300. This force feedback, in turn, is communicated to power-pack 120, e.g., a processor and associated memory of main controller circuit board 126b to, in turn, direct the appropriate motor controller of motor controller circuit board 126a to set the speed current limit on the appropriate motor 128 to ensure closing and firing forces are maintained within acceptable limits. Circuit board 224 further includes a memory configured to store data relating to adapter assembly 200, e.g., identifying information, life-cycle information, system information, force information, which may likewise be communicated to power-pack 120.

Figure 4:
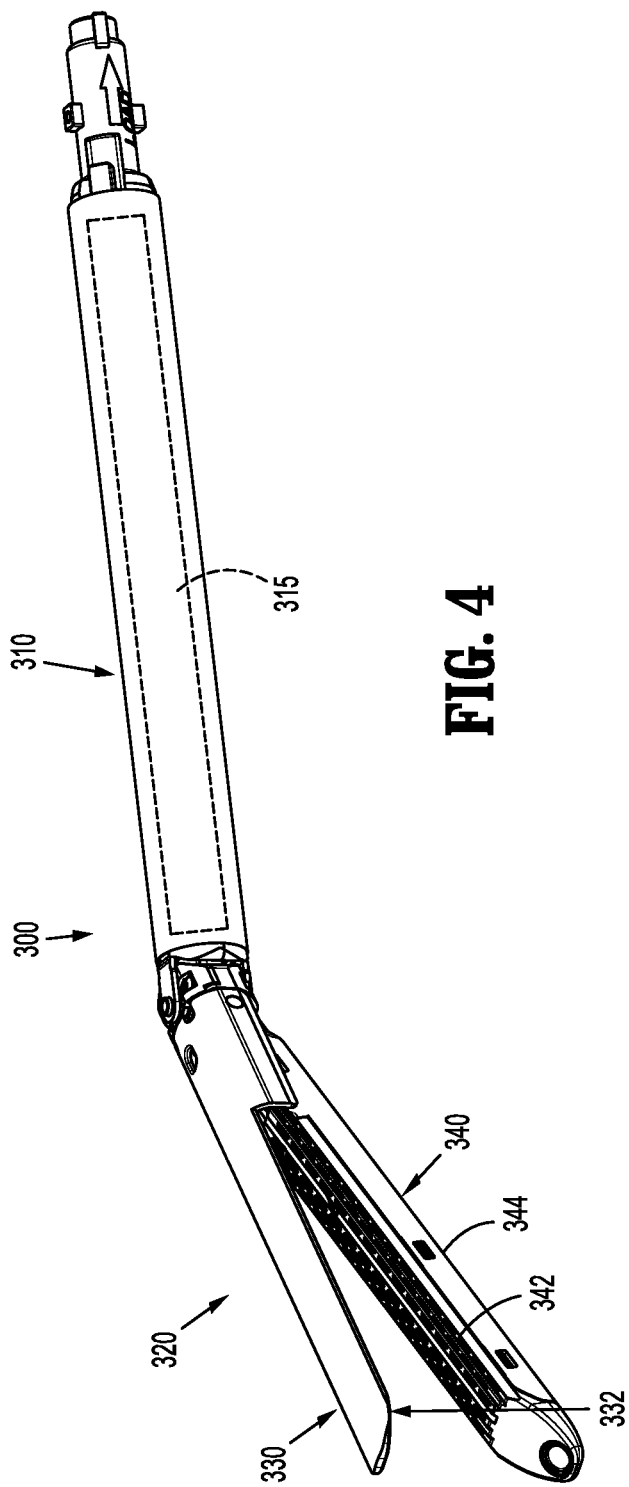
FIG. 4 is a perspective view of the end effector of the surgical device of FIG. 1.

Referring to FIG. 4, end effector 300 is in the form of a linear-stapling, single use loading unit. It should be understood, however, that other types of end effectors may also be used with surgical device 10 of the present disclosure including, for example, end-to-end anastomosis loading units, multi-use loading units, transverse loading units, and curved loading units. The particular end effector 300 utilized with surgical device 10 is recognized by power-pack 120 of handle assembly 100 to enable appropriate operation thereof.

End effector 300 includes a proximal body portion 310 and a tool assembly 320. Proximal body portion 310 is configured to releasably attach to the distal end portion of adapter assembly 200 and tool assembly 320 is pivotally attached to proximal body portion 310. Tool assembly 320 includes an anvil assembly 330 and a cartridge assembly 340. Anvil and cartridge assemblies 330, 340 are pivotal with respect to each other such that tool assembly 320 is movable between an open or unclamped position and a closed or clamped position.

Anvil assembly 330 includes an anvil plate 332 defining a tissue contacting surface (not shown) having a plurality of staple forming pockets (not shown) and a longitudinal slot (not shown) defined therein. Cartridge assembly 340 includes a staple cartridge 342 and a cartridge carrier 344. Staple cartridge 342 defines a tissue contacting surface having staple pockets formed therein for receiving a plurality of staples (not shown) and a longitudinal slot formed in and extending along a substantial length of staple cartridge 342. Cartridge carrier 344 defines an elongated support channel configured to selectively receive staple cartridge 342 therein.

Proximal body portion 310 of end effector 300 includes a drive assembly 315 operably associated with and slidably disposable between anvil and cartridge assemblies 330, 340. Drive assembly 315 includes a drive component, e.g., an elongated drive beam extending to an I-beam including a knife. The I-beam is configured to engage anvil and cartridge assemblies 330, 340 and, upon distal translation relative thereto, pivot anvil and cartridge assemblies 330, 340 relative to one another to close end effector 300 to clamp tissue between the tissue-contacting surfaces of anvil and cartridge assemblies 330, 340. The I-beam is further configured to translate through the longitudinal channels of anvil and cartridge assemblies 330, 340 to drive a sled (not shown) that urges the staples from staple cartridge 342, through clamped tissue, into the staple forming pockets of anvil assembly 330 to fire end effector 300 and form the staples about the clamped tissue. The knife of the I-beam travels through the longitudinal slots defined through anvil and cartridge assemblies 330, 340, to longitudinally cut the clamped and stapled tissue during firing of end effector 300. Drive assembly 315 is operably associated with distal drive member 250 of adapter assembly 200 such that distal translation of distal drive member 250 (effected by a first rotational output received from one of the motors 128 of power-pack 120), is imparted to drive assembly 315 to drive the I-beam to close and fire end effector 300. Proximal translation of distal drive member 250 (effected by a second, opposite rotational output received from one of the motors 128 of power-pack 120), on the other hand, serves to retract drive assembly 315 proximally to return the I-beam to its initial position and open end effector 300 to release the stapled and cut tissue.

For a more detailed discussion of the construction and operation of end effector 300, as illustrated in FIGS. 1 and 4, reference may be made to U.S. Pat. No. 7,819,896, filed on Aug. 31, 2009, entitled "TOOL ASSEMBLY FOR A SURGICAL STAPLING DEVICE," the entire contents of which being incorporated by reference herein.

Referring generally to FIGS. 1-4, as noted above, distal translation (extension) of distal drive member 250 of adapter assembly 200 is imparted to drive assembly 315 of end effector 300 to close and fire end effector 300. As also noted above, power-pack 120 controls one of the motors 128 to provide a rotational output to adapter assembly 200 that, in turn, is converted (via the corresponding force/rotation transmitting/converting assembly of adapter assembly 200) into distal translation of distal drive member 250 and, thus, drives the closure and firing of end effector 300. More specifically, Power-pack 120, e.g., a processor and associated memory of main controller circuit board 126b, receives force feedback from strain gauge 226 of adapter assembly 200 (via circuit board 224) to set the speed current limit on the corresponding motor 128 to ensure clamping and firing forces are maintained within acceptable limits. Thus, feedback-based control is effectuated whereby the speed of motor 128 may be increased, decreased, or maintained at different points during a clamping and firing operation based upon the clamping and firing forces encountered, as reported by strain gauge 226.

Once firing is completed and it is desired to retract drive assembly 315 and open end effector 300 to release the stapled and cut tissue, power-pack 120 drives one of the motors 128 to provide a rotational output to adapter assembly 200 that, in turn, is converted (via the corresponding force/rotation transmitting/converting assembly of adapter assembly 200) into proximal translation (retraction) of distal drive member 250. This proximal translation of distal drive member 250, as noted above, drives the retraction of drive assembly 315 and opening of end effector 300. However, neither strain gauge 226 nor any other components of end effector 300 or adapter assembly 200 provides force feedback to power-pack 120 during retraction of drive assembly 315 and, thus, feedback-based control as provided during closing and firing of end effector 300 is not available during retraction.

It has been found that controlling retraction of drive assembly 315 is important to manage retraction forces and thereby prevent system damage or malfunction. On the other hand, it is desirable to minimize retraction time to decrease the lengths of surgical procedures and, thus, the time patients are required to remain under anesthesia. However, as noted above, feedback-based control as provided during closing and firing is not available during retraction.

In order to control retraction to manage retraction forces while minimizing retraction time, the force-feedback from strain gauge 226 used to control closing/firing is utilized during retraction, thus obviating the need for retraction force-feedback. More specifically, a memory associated with a processor of main controller circuit board 126b of power-pack 120 (or other suitable memory associated with power-pack 120) is configured to store the force profile (based upon information received from strain gauge 226) and/or motor speed profile (based upon the control of the appropriate motor 128 based upon the force-feedback from strain gauge 226) during closing and firing so that the profile may be utilized to control retraction.

Figure 5A:
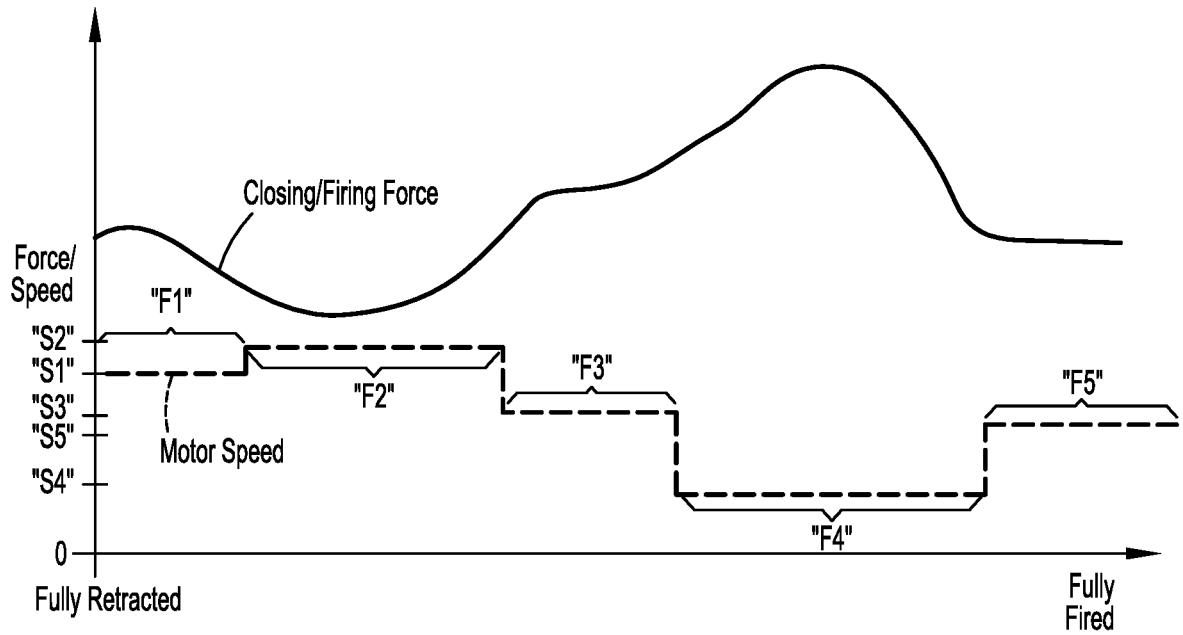
FIG. 5A is a graph illustrating exemplary force and motor speed curves during closing and firing of the surgical device of FIG. 1.

With additional reference to FIG. 5A, sample force and motor speed profiles (for illustrative purposes) for closing/firing are provided. As illustrated, motor 128 is initially driven at a first speed "S1" for an initial, first portion of closing/firing "F1." In response to decreased forces, the speed of the motor 128 is increased to a second speed "S2" during a second portion of closing/firing "F2." A subsequent increase in force causes the motor 128 to be decreased from the second speed "S2" to a third speed "S3" during a third portion of closing/firing "F3." Still further increases in force cause the motor 128 to be decreased to a fourth sped "S4" during a fourth portion "F4" of closing/firing. Finally, a decrease in force causes the motor 128 to increase in speed from the fourth speed "S4" to a fifth speed "S5" during a fifth and final portion of closing/firing "F5."

Figure 5B:
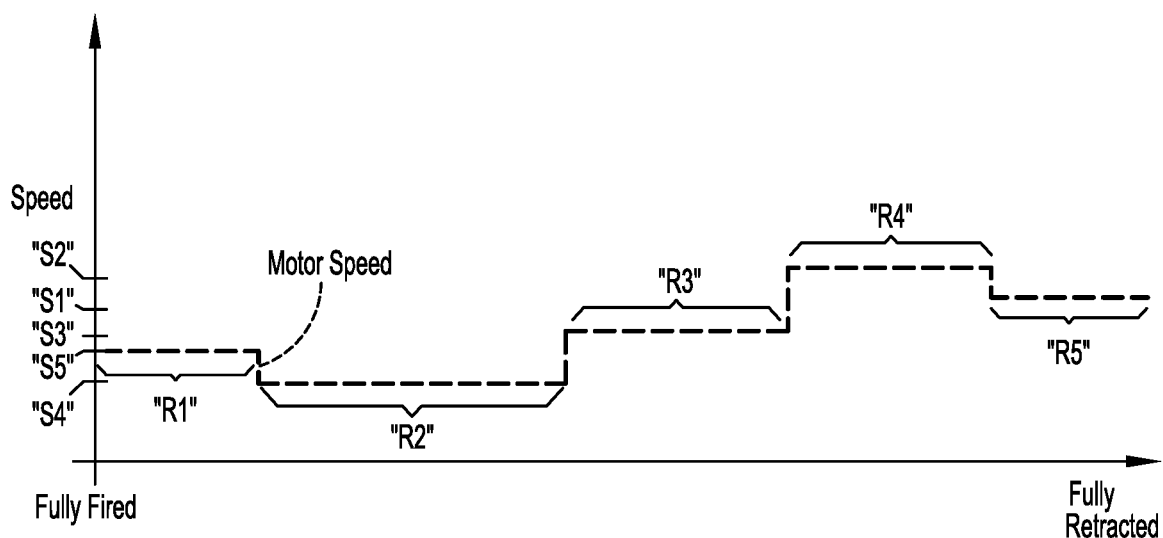
FIG. 5B is a graph illustrating an exemplary motor speed curve during retraction of the surgical device of FIG. 1.

Referring also to FIG. 5B, a sample motor speed profile for retraction based upon the sample force and/or motor speed profiles (see FIG. 5A) for closing/firing is provided. As illustrated in FIG. 5B, motor speed is controlled during retraction to account for the portions of retraction where increased forces are likely to be met and/or where decreased motor speeds are likely to be needed, based upon the closing/firing force profile and/or the closing/firing motor speed profile (see FIG. 5A). As understood, retraction is effected in an opposite direction as closing/firing and, thus, the retraction motor speed profile correlates oppositely to the closing/firing motor speed profile. Similarly, the retraction motor speed profile may correlate oppositely with the closing/firing force profile. More specifically, during an initial, first portion "R1" of retraction, which corresponds to the final, fifth portion "F5" of closing/firing, the motor is set to speed "S5." During a second portion "R2" of retraction, which corresponds to the fourth portion "F4" of closing/firing, the motor is set to speed "S4." During a third portion "R3" of retraction, corresponding to the third portion "F3" of closing/firing, the motor is set to speed "S3." During a fourth portion "R4" of retraction, corresponding to the second portion "F2" of closing/firing, the motor is set to speed "S2." During a final, fifth portion "R5" of retraction, corresponding to the initial, first portion "F1" of closing/firing, the motor is set to speed "S1." Thus, the motor speed is adjusted to account for the portions of retraction where increased forces may be encountered since increased forces were sensed in the corresponding portions of closing/firing, without the need for force feedback during retraction.

Although illustrated as having the motor speeds directly correspond in FIGS. 5A and 5B, the motor speed of the retraction profile need not correspond 1:1 to the motor speed of the closing/firing profile. For example, a scale factor may be introduced to increase or decrease the motor speed during retraction (or portions thereof) as compared to closing/firing; a dampening or strengthening coefficient may be provided to lessen or exaggerate changes in motor speed during retraction (or portions thereof) as compared to closing/firing; upper and/or lower limits in retraction speed may be imposed regardless of the corresponding motor speed during closing firing; and/or other override rules may be implemented. Additionally or alternatively, the firing speed during closing/firing and/or during retraction may be adjusted between two or more incremental settings (e.g., HIGH and LOW; HIGH, MEDIUM, and LOW; etc.) (which may be the same or different between closing/firing and retraction), or may be adjusted continuously during closing/firing and/or during retraction between upper and lower limits (which may be the same or different between closing/firing and retraction).

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A powered handheld electromechanical surgical device, comprising:
    a motor configured to drive extension and retraction of a drive component;
    a sensor configured to sense force exerted on the drive component during extension of the drive component; and
    a controller including a processor and a non-transitory computer-readable storage medium storing instructions that, when executed by the processor, cause the processor to:
        receive the sensed force from the sensor;
        control a speed of the motor during extension of the drive component in accordance with the sensed force;
        generate a speed profile based on the speed of the motor controlled during extension of the drive component from a fully retracted position to a fully extended position, wherein the speed profile includes a plurality of portions corresponding to accelerations in motor speed and at least one portion corresponding to a deceleration in motor speed; and
        control a speed of the motor during retraction of the drive component from the fully extended position to the fully retracted position to replicate the generated speed profile in reverse.

2. The powered handheld electromechanical surgical device according to claim 1, further comprising:
    a handle assembly including the motor and controller disposed therein; and
    an adapter assembly releasably engaged with the handle assembly and including the drive component and sensor disposed therein.

3. The powered handheld electromechanical surgical device according to claim 2, further comprising an end effector releasably engaged with the adapter assembly, wherein extension of the drive component at least one of closes or fires the end effector, and wherein retraction of the drive component opens the end effector.

4. The powered handheld electromechanical surgical device according to claim 1, wherein the sensor is a strain gauge.

5. The powered handheld electromechanical surgical device according to claim 1, wherein the motor provides a rotational output, and wherein the rotational output is converted into translation of the drive component to extend and retract the drive component.

6. A powered handheld electromechanical surgical device, comprising:
    a motor configured to drive extension and retraction of a drive component;
    a sensor configured to sense force exerted on the drive component during extension of the drive component; and
    a controller including a processor and a non-transitory computer-readable storage medium storing instructions that, when executed by the processor, cause the processor to:
        receive the sensed force from the sensor;
        control a speed of the motor during extension of the drive component in accordance with the sensed force;
        generate a force profile during extension of the drive component from a fully retracted position to a fully extended position, wherein the force profile includes a plurality of decreases in force and at least one increase in force; and
        control a speed of the motor, in accordance with a speed profile, during retraction of the drive component from the fully extended position to the fully retracted position in accordance with the generated force profile in reverse, such that a plurality of portions of the speed profile corresponding to decelerations in motor speed and at least one-portion of the speed profile corresponding to an acceleration motor speed of the motor during retraction coincide with the plurality of decreases in force and the at least one increase in force, respectively, of the generated force profile in reverse.

7. The powered handheld electromechanical surgical device according to claim 6, further comprising:
    a handle assembly including the motor and controller disposed therein; and
    an adapter assembly releasably engaged with the handle assembly and including the drive component and sensor disposed therein.

8. The powered handheld electromechanical surgical device according to claim 7, further comprising an end effector releasably engaged with the adapter assembly, wherein extension of the drive component at least one of closes or fires the end effector, and wherein retraction of the drive component opens the end effector.

9. The powered handheld electromechanical surgical device according to claim 6, wherein the sensor is a strain gauge.

10. The powered handheld electromechanical surgical device according to claim 6, wherein the motor provides a rotational output, and wherein the rotational output is converted into translation of the drive component to extend and retract the drive component.

11. A method of controlling a powered handheld electromechanical surgical device, comprising:
   activating a motor to drive extension of a drive component;
   sensing force exerted on the drive component during extension of the drive component;
   controlling a speed of the motor during extension of the drive component in accordance with the sensed force;
   generating a speed profile during extension of the drive component from a fully retracted position to a fully extended position, wherein the speed profile includes a plurality of portions corresponding to accelerations in motor speed and at least one portion corresponding to a deceleration in motor speed; and
   controlling a speed of the motor during retraction of the drive component from the fully extended position to the fully retracted position to replicate the generated speed profile in reverse.

* * * * *